(12) United States Patent
Norvell

(10) Patent No.: US 12,115,236 B1
(45) Date of Patent: Oct. 15, 2024

(54) TATTOO INK FORMULATION AND METHOD

(71) Applicant: Michelle Norvell, Las Vegas, NV (US)

(72) Inventor: Michelle Norvell, Las Vegas, NV (US)

( * ) Notice: Subject to any disclaimer, the term of this patent is extended or adjusted under 35 U.S.C. 154(b) by 170 days.

(21) Appl. No.: 17/981,967

(22) Filed: Nov. 7, 2022

(51) Int. Cl.
*A61Q 1/02* (2006.01)
*A61K 8/04* (2006.01)
*A61K 8/19* (2006.01)
*A61Q 1/00* (2006.01)

(52) U.S. Cl.
CPC .............. *A61K 8/044* (2013.01); *A61K 8/19* (2013.01); *A61Q 1/025* (2013.01); *A61K 2800/43* (2013.01)

(58) Field of Classification Search
CPC .............. A61K 9/0014; A61K 2800/43; A61K 49/0091; A61K 2800/652; A61Q 1/025; A61Q 1/02; A61Q 19/00
See application file for complete search history.

(56) References Cited

U.S. PATENT DOCUMENTS 6,013,122 A * 1/2000 Klitzman ............... A61Q 19/04
106/31.03
2021/0154107 A1* 5/2021 Shah ...................... A61K 8/90

FOREIGN PATENT DOCUMENTS

WO   WO-2022212691 A1 * 10/2022

* cited by examiner

*Primary Examiner* — Tracy Liu
(74) *Attorney, Agent, or Firm* — Gulf Coast Intellectual Property Group

(57) ABSTRACT

A tattoo ink formulation method that employs utilization of glass microspheres to create a tattoo ink that can be removed if desired by an individual having a tattoo created with the tattoo ink. The present invention employs a first and second embodiment both utilizing glass microspheres to create a tattoo ink. The tattoo ink of the present invention is operable to be removed from a user through utilization of ultrasound. The first embodiment of the present invention employs an organic dye having an affinity for glass and as such is deposited onto the surface of the glass microspheres when immersed in a solution. The second embodiment of the present invention includes treatment of the glass microspheres in order to render the surface thereof hydrophobic. Ensuing treatment of the glass microspheres the glass microspheres are immersed in a solution containing an organic dye with limited solubility to create a tattoo ink.

6 Claims, 2 Drawing Sheets

TATTOO INK FORMULATION AND METHOD

FIELD OF THE INVENTION

The present invention relates generally to tattooing, more specifically but not by way of limitation, a method of preparing a tattoo ink that can be removed wherein the present invention employs utilization of glass microspheres having a hydrophobic surface with a organic dye deposited thereonto.

BACKGROUND

As is known in the art, tattooing goes back as far as back as Neolithic times. Ancient tattooing was performed for various cultural and religious reasons and utilized primitive tools such as fish bones to pierce the skin and apply ink thereto. The word tattoo is derived from the Tahitian word, tatau, and was introduced into the English language subsequent one of Captain James Cook's expeditions to the South Pacific. Over the past three decades tattooing has become more popular in the United States and the practice has crossed social boundaries and having a tattoo is considered more socially acceptable than in the past. Artists create tattoos by injecting ink into a person's skin. To accomplish this the artist will utilize a needle that punctures skin at a rate of 50 to 3000 times per minute. The needle typically is calibrated to penetrate the skin about a millimeter and deposits a drop of insoluble ink.

One issue with tattooing is the permanence of the ink. Once an individual chooses to have a tattoo it is permanent and if desired to be removed can be a painful and costly procedure. Tattoo inks are manufactured from materials such as but not limited to titanium dioxide. These materials are designed to be permanent. If a person decides they no longer wish to have the tattoo, the removal procedure can be expensive and painful. The standard modality for tattoo removal involves the utilization of Q-switched lasers. The laser has been proven to be generally successful at removing most pigments but the patient still endures a significant amount of discomfort during the removal process.

It is intended within the scope of the present invention to provide a tattoo ink formulation having an ability for removal thereof subsequent application of a tattoo wherein the tattoo ink formulation of the present invention includes utilization of an organic dye loaded onto the surface of glass microspheres wherein the microspheres are suspended in a solution to create a tattoo ink.

SUMMARY OF THE INVENTION

It is the object of the present invention to provide an erasable tattoo ink utilizing glass microspheres wherein the present invention provides a method that includes a step of surface loading glass microspheres through suspension in water and organic dye solution.

Another object of the present invention is to provide a method for creating an erasable tattoo ink wherein an embodiment of the present invention includes wherein organic dyes employed have an affinity for glass.

A further object of the present invention is to provide an erasable tattoo ink utilizing glass microspheres wherein the method of the present invention includes a step of drying microspheres subsequent exposure to a aqueous solution of dye.

Still another object of the present invention is to provide a method for creating an erasable tattoo ink wherein a tattoo ink is created through suspension of microspheres having dye loaded onto the surfaces thereof in water.

An additional object of the present invention is to provide an erasable tattoo ink utilizing glass microspheres wherein the method of the present invention wherein the water having the suspension of glass microspheres can have a polymer added thereto for increase of viscosity of the dye solution.

Yet a further object of the present invention is to provide a method for creating an erasable tattoo ink wherein an embodiment of the present invention includes modification of the surface of glass microspheres to render the surface hydrophobic.

Another object of the present invention is to provide an erasable tattoo ink utilizing glass microspheres wherein the method of the present invention includes exposing the surface of the glass microspheres to an inert gas.

An alternate object of the present invention is to provide a method for creating an erasable tattoo ink wherein the glass microspheres are exposed to a dry solvent.

Still a further object of the present invention is to provide an erasable tattoo ink utilizing glass microspheres wherein the method of the present invention includes a step of exposing the glass microspheres to a long chain linear aliphatic alkylating agent.

A further object of the present invention is to provide a method for creating an erasable tattoo ink that further includes collecting the exposed glass microspheres via filtration.

An alternative objective of the present invention is to provide an erasable tattoo ink utilizing glass microspheres wherein the method of the present invention includes a step of quenching a reaction with an injection of alcohol.

Another object of the present invention is to provide a method for creating an erasable tattoo ink that further includes a step of rinsing the surface modified glass microspheres with hexane.

Yet a further object of the present invention is to provide an erasable tattoo ink utilizing glass microspheres wherein the method of the present invention includes immersing the surface modified glass microspheres into an aqueous solution of organic dye having limited solubility in water.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
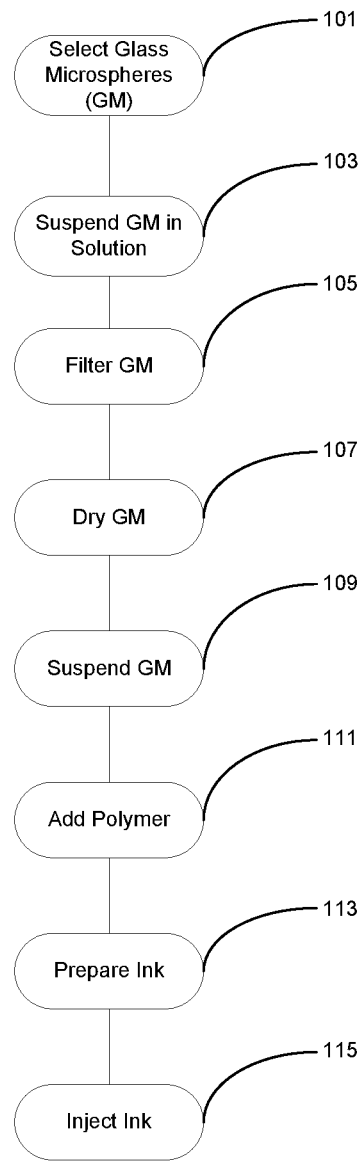
FIG. 1 is a flowchart of the first embodiment of the method of the present invention.

Referring now to the drawings submitted herewith, wherein various elements depicted therein are not necessarily drawn to scale and wherein through the views and figures like elements are referenced with identical reference numerals, there is illustrated a tattoo ink formulation method 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Referring now to the drawings submitted as a part hereof, in FIG. 1 a diagram of the tattoo ink formulation method 100 in a first embodiment is illustrated therein. In step 101, a user will select a quantity of glass microspheres. While various sizes and types of glass microspheres can be employed in the tattoo ink formulation method 100, it is contemplated within the scope of the present invention that the glass microspheres employed within the tattoo ink formulation method 100 have a size of eighteen to sixty-five microns with a surface area range of 1.9 to 2.7 $m^2/g$. Step 103, the glass microspheres are suspended in a solution. The solution in which the glass microspheres are suspended is a solution of water and an organic dye wherein the organic dye has an affinity for glass. It is contemplated within the scope of the present invention that the glass microspheres are suspended for at least an hour in the solution.

In step 105, subsequent exposure to the solution, the solution is filtered so as to capture the glass microspheres now having the organic dye deposited on the surface thereof. Step 107, after filtering the glass microspheres, the glass microspheres are dried wherein the drying of the glass microspheres occurs at a temperature between fifty an sixty degrees centigrade. In step 109, ensuing drying of the glass microspheres, the glass microspheres are utilized to create a tattoo ink by suspending a quantity of the dyed glass microspheres in water. Step 111, the water having the dyed glass microspheres therein has the viscosity thereof increased through addition of a polymer. Polymers such as but not limited to xanthan gum, carrageenan and other synthetic polymers can be employed to provide an increase of the viscosity of the tattoo ink so as to make suitable for injection in the subcutaneous layer of an individual. Step 113, the tattoo ink is injected into an individual in the desired location.

Figure 2:
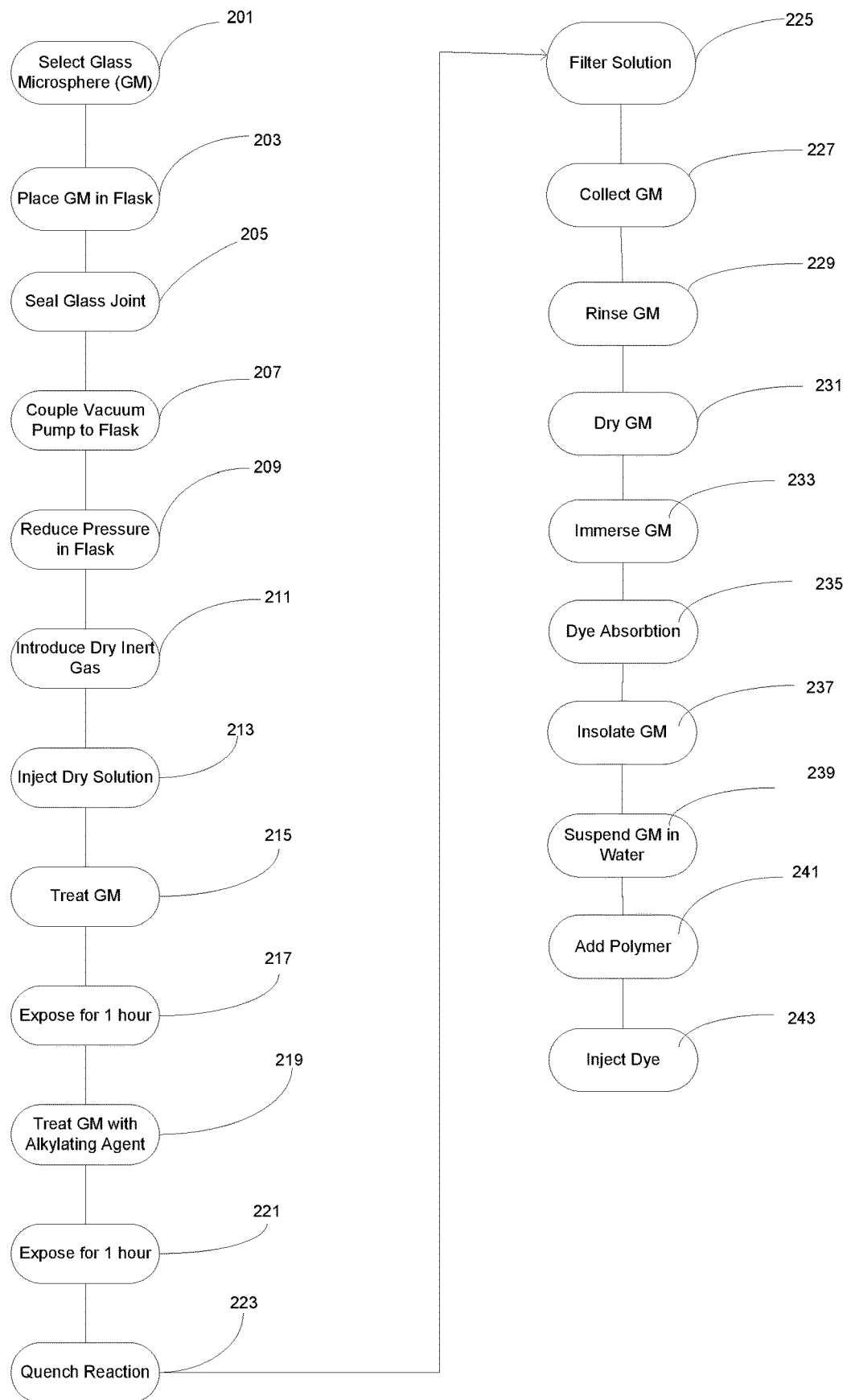
FIG. 2 is a flowchart of a second embodiment of the method of the present invention.

Now referring to FIG. 2 herein, a second embodiment of the tattoo ink formulation method 100 is diagrammed therein. In step 201, a user of the tattoo ink formulation method 100 will select a desired quantity of glass microspheres. While various sizes and types of glass microspheres can be employed in the tattoo ink formulation method 100, it is contemplated within the scope of the present invention that the glass microspheres employed within the tattoo ink formulation method 100 have a size of eighteen to sixty-five microns with a surface area range of 1.9 to 2.7 $m^2/g$. Step 203, the glass microspheres are placed in a flask. In a preferred embodiment of the present invention the glass microspheres are placed in a flask having a glass valve and a ground glass joint at the neck of the flask. In step 205 the glass joint at the neck of the flask is sealed. Step 207, the flask is operably coupled to a vacuum pump. In step 209, the vacuum pump is activated in order to evacuate all of the atmospheric air within the interior volume of the flask.

In step 211, an inert gas is introduced into the interior volume of the flask. By way of example but not limitation, nitrogen gas can be employed in this step. Step 213, subsequent introduction of an inert gas, a dry solvent is injected into the interior volume of the flask. It is contemplated within the scope of the present invention that the dry solvent could be but is not limited to tetrahydrofuran. In step 215, the glass microspheres are further treated with a strong base such as but not limited to n-butyl lithium. Step 217, the glass microspheres are exposed to the aforementioned for at least one hour. It should be understood within the scope of the present invention that the glass microsphere exposure could be more or less than an hour. In step 219, afterwards, the glass microspheres are treated with an alkylating agent. By way of example but not by limitation, the alkylating agent can be a long chain linear aliphatic alkylating agent such as but not limited to 1-bromohexadecane. Step 221, the glass microspheres are exposed to the alkylating agent for at least one hour. In step 223, the instant reaction within the flask is quenched. In a preferred embodiment of the present invention the reaction is quenched via injection of an alcohol such as but not limited to ethanol into the flask. Step 225, the solution is filtered utilizing suitable techniques. In step 227, as the solution is filtered the glass microspheres are captured. Step 203 through step 227 have produced a surface modification on the glass microspheres wherein the surface of the glass microspheres are hydrophobic. In step 229, the glass microspheres are rinsed wherein the rinsing is performed with a solvent such as but not limited to hexane.

Step 231, the glass microspheres are dried wherein a preferred drying of the glass microspheres occurs at room temperature in a fume hood. In step 233, the glass microspheres are immersed in an aqueous solution. Step 235, the immersion of the glass microspheres in the aqueous solution of water and an organic dye (wherein the organic dye has limited solubility in water) will result in the organic dye being deposited onto the hydrophobic surface layer of the glass microspheres. In step 237, the glass microspheres now having organic dye on the surface thereof are isolate via filtration of the solution and subsequently dried. Step 239, following the drying of the glass microspheres, the glass microspheres are suspended in water. In step 241, a polymer is added to increase the viscosity of the water having the glass microspheres suspended therein to a suitable viscosity for use as tattoo ink. Step 243, the tattoo ink is injected into an individual in a desired area.

The tattoo ink formulation method 100 creates a usable tattoo ink employing either the first embodiment or the second embodiment discussed herein above. The tattoo ink for both the first embodiment and the second embodiment can be removed from the skin of the user through utilization of ultrasound. If a user having a tattoo that employed tattoo ink of the present invention desires to have the tattoo removed from the skin, exposure to ultrasound to the area of the tattoo will disintegrate the ink having the glass microspheres and result in the disappearance of the tattoo.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding description is, therefore, not intended to be limited to the specific forms set forth herein, but on the contrary, it is intended to cover such alternatives, modifications, and equivalents, as can be reasonably included within the spirit and scope of the invention.

What is claimed is:

1. A method for creation of a tattoo ink that is configured to be removed if desired by a recipient of a tattoo created by the tattoo ink wherein the method comprises the steps of:
   selecting a quantity of glass microspheres;
   placing said glass microspheres within an interior volume of a vessel, wherein the vessel is a flask;
   sealing the vessel from atmospheric air;
   vacuuming the interior volume of the vessel so as to remove the atmospheric air;
   introducing an inert gas into the interior volume of the vessel;
   injecting a dry solvent into the interior volume of the vessel;
   treating the glass microspheres disposed in the interior volume of the vessel with a base;
   exposing said glass microspheres to an alkylating agent;
   quenching a reaction within the interior volume of the vessel;
   collecting the glass microspheres from the interior volume of the vessel, wherein the glass microspheres have surface that is hydrophobic;
   immersing the glass microspheres in a solution of organic dye and water, wherein the organic dye is deposited on the surface of the glass microsphere;
   isolating said glass microspheres having the organic dye deposited onto the hydrophobic surface thereof;
   suspending the glass microspheres in water to create a tattoo ink.

2. The method for creation of a tattoo ink that is configured to be removed if desired by the recipient of a tattoo created by the tattoo ink as recited in claim 1, further including a step of adding a polymer, said polymer added to the water having the glass microspheres suspended therein, and wherein said polymer is operable to increase a viscosity of the water.

3. The method for creation of a tattoo ink that is configured to be removed if desired by the recipient of a tattoo created by the tattoo ink as recited in claim 2, wherein the glass microspheres are treated with the dry solvent for at least one hour.

4. The method for creation of a tattoo ink that is configured to be removed if desired by the recipient of a tattoo created by the tattoo ink as recited in claim 3, wherein the alkylating agent is a long chain linear aliphatic alkylating agent.

5. The method for creation of a tattoo ink that is configured to be removed if desired by the recipient of a tattoo created by the tattoo ink as recited in claim 4, wherein the glass microspheres are treated with the alkylating agent for at least one hour.

6. The method for creation of a tattoo ink that is configured to be removed if desired by the recipient of a tattoo created by the tattoo ink as recited in claim 5, wherein the base utilized to treat the glass microspheres is n-butyl lithium dissolved in hexane.

\* \* \* \* \*